__ United States Patent [19]

Adams et al.

[11] 4,052,514
[45] * Oct. 4, 1977

[54] TRIHALOSUBSTITUTED BIPHENYLYL PROPIONIC ACIDS

[75] Inventors: Stewart S. Adams, Redhill; Bernard J. Armitage; John S. Nicholson, both of Beeston, all of England

[73] Assignee: The Boots Company Limited, England

[*] Notice: The portion of the term of this patent subsequent to Jan. 13, 1993, has been disclaimed.

[21] Appl. No.: 397,604

[22] Filed: Sept. 14, 1973

Related U.S. Application Data

[63] Continuation-in-part of Ser. No. 235,825, March 17, 1972, abandoned.

[30] Foreign Application Priority Data

Sept. 22, 1972 United Kingdom ............ 44013/72
Mar. 26, 1971 United Kingdom ............ 7936/71

[51] Int. Cl.² .............. A61K 31/19; A61K 31/205; A61K 31/215; C07C 63/33

[52] U.S. Cl. .................. 424/316; 544/161; 260/307 F; 260/465 G; 260/500.5 H; 260/501.16; 260/515 A; 260/515 P; 260/518 A; 260/551 R; 260/558 R; 260/558 S; 260/558 A; 260/611 A; 260/618 A; 424/308; 424/315; 424/317; 424/324; 424/345; 560/101; 560/36; 560/21; 560/82; 560/14

[58] Field of Search .............. 260/515 A, 469; 424/308, 317, 316

[56] References Cited

U.S. PATENT DOCUMENTS

| | | | |
|---|---|---|---|
| 3,624,142 | 11/1971 | Shen et al. | 260/515 |
| 3,792,170 | 2/1974 | Shen et al. | 424/303 |
| 3,901,906 | 8/1975 | Kozlik | 260/307 F |
| 3,932,499 | 1/1976 | Adams et al. | 260/469 |

FOREIGN PATENT DOCUMENTS 1,091,403  11/1967  United Kingdom ............ 260/515

*Primary Examiner* — Jane S. Myers
*Attorney, Agent, or Firm* — Gordon W. Hueschen

[57] ABSTRACT

Novel trihalosubstituted biphenylyl propionic and acetic acids and their derivatives are described together with processes for their preparation and composition of them. They are useful as anti-inflammatory agents.

20 Claims, No Drawings

TRIHALOSUBSTITUTED BIPHENYLYL PROPIONIC ACIDS

This application is a continuation-in-part application of Ser. No. 235,825 filed Mar. 17, 1972, now abandoned.

This invention relates to novel substituted propionic acids, and derivatives thereof, that have valuable biological properties, in particular anti-inflammatory properties.

It is now well known that certain substituted propionic acids are valuable anti-inflammatory agents. For example 2-(4-isobutylphenyl)propionic acid is now being widely used as an anti-inflammatory agent and also is effective as an analgesic and anti-pyretic compound. More recently it has been proposed to use 2-(substituted biphenylyl)propionic acids for rather similar purposes. For example a large number of such compounds are disclosed generically, and some are named specifically, in British patent specifications Nos. 1,091,403 and 1,116,432. Among the most effective compounds disclosed in those specifications is 2-(2-fluoro-4-biphenylyl)propionic acid. It will be observed that most of the known biphenylyl compounds disclosed as anti-inflammatory agents have mono substitution in the biphenylyl radical although some are disubstituted.

The known activity of the known substituted biphenylyl propionic acids has been a short term activity in the sense that after administration the compound remains in the bloodstream, and therefore available to exert a therapeutic effect, for only a very short time, for example a few hours, for example 3 to 6 hours, at the most. Accordingly when the compounds are being used for treating chronic conditions it has been considered necessary to administer them several times a day.

Our object has been to produce novel compounds having particularly desirable long lasting anti-inflammatory activity, to produce pharmaceutical compositions of such compounds and processes for the production of such compounds and methods of treating conditions of prolonged inflammation.

Novel compounds according to the invention have general formula I

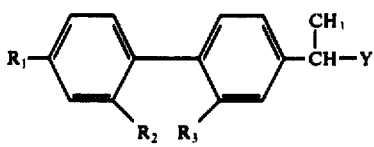

in which $R_1$, $R_2$ and $R_3$ are individually selected from fluorine, chlorine and bromine, Y is COOH, CONH$_2$, CH$_2$OH or CONHOH together with pharmaceutically acceptable esters (i.e. compounds wherein Y is COOR$_4$ in which R$_4$ is an esterifying radical), inorganic salts and organic salts of those compounds wherein Y is COOH, and inorganic salts wherein Y is CONHOH.

All the compounds of the invention have long acting activity. Naturally the degree of activity exerted by any particular compound and the duration of activity will vary from compound to compound, depending upon the substituents $R_1$, $R_2$ and $R_3$ and may also vary depending upon the value of Y. The preferred compounds are those wherein Y is COOH. It is believed that when salts, esters, amides or alcohols and hydroxamic acids are used in place of the acids the derivatives are metabolised by the animal body and are converted in the body into the corresponding acids.

Preferred compounds of the invention have at least one of $R_1$, $R_2$ and $R_3$ representing fluorine, and most preferably they have at least two of the radicals $R_1$, $R_2$ and $R_3$ representing fluorine with the other radical representing fluorine or chlorine. Accordingly the most preferred compounds are the difluoromonochloro compounds and the trifluoro compound, the latter being particularly advantageous. Thus the preferred compounds are 2-(2,2',4'-trifluoro-4-biphenylyl)propionic acid, 2-(4'-chloro-2,2'-difluoro-4-biphenylyl)propionic acid, 2-(2'-chloro-2,4'-difluoro-4-biphenylyl)propionic acid and 2-(2-chloro-2',4'-difluoro-4-biphenylyl)propionic acid, as well as the various derivatives of these acids wherein the carboxyl group is replaced by one of the other values for Y listed above, and the salts of these acids and of the hydroxamic acids.

In addition to having long acting activity as anti-inflammatory agents, much longer for example than 2-(4-isobutylphenyl)propionic acid and 2-(2-fluoro-4-biphenylyl)propionic acid, the compounds of the invention also possess analgesic and antipyretic properties.

The half-life of the compounds of the invention in the blood of the subject to which they are administered is a good indication of their duration of activity. The half-life may be measured by giving oral doses of the compounds and determining levels in the plasma at various times thereafter (see, for example, Ritschel, W. A., *Drug Intell. clin. Pharmacy*, 1970, 4, 332.).

The best method of indicating long acting anti-inflammatory activity of the compounds is by means of a test in which compounds are administered chronically e.g. the rat adjuvant arthritis test. Acute tests of measuring anti-inflammatory activity, such as the carageenin oedema and the ultra-violet erythema test are not a true indication of long acting anti-inflammatory activity since such acute tests are not of sufficiently long duration to reflect and demonstrate the long-acting effect of the compounds. The adjuvant arthritis test conducted on the rat is, however a chronic test and is believed to give a good indication of the effectiveness of the compounds for the treatment of chronic conditions in humans. The adjuvant arthritis test is described by Newbould, B. B., in *Br. J. Pharmac. Chemother.*, 1963, 21, 127. In the test arthritis is produced by injecting intradermally into the tail 0.1 ml. of a suspension of killed human tubercle bacilli (6 mg./ml.) in liquid paraffin BP. A polyarthritis develops over the next 3 weeks in untreated controls. The compounds under test (vehicle only for control animals) are given daily by mouth from the day the adjuvant is injected for 21 days. On day 21 the degree of arthritis is assessed on each hind foot. The degree of inhibition produced by a compound is estimated by comparison of the total arthritic scores with those found in the controls.

In the following Table are given the results in the adjuvant arthritis test for the four preferred compounds of the invention and 2-(2-fluoro-4-biphenylyl)propionic acid, the latter compound being used as a standard of reference in the adjuvant arthritis test.

TABLE I

| COMPOUND | ADJUVANT ARTHRITIS |
|---|---|
| 2-(2,2',4'-trifluoro-4-biphenylyl)propionic acid | >>10 |
| 2-(4'-chloro-2,2'-difluoro 4-biphenylyl)propionic acid | >3 |

TABLE I-continued

| COMPOUND | ADJUVANT ARTHRITIS |
|---|---|
| 2-(2'-chloro-2,4'-difluoro-4-biphenylyl)propionic acid | >3 |
| 2-(2-chloro-2',4'-difluoro-4-biphenylyl)propionic acid | >10 |
| 2-(2-fluoro-4-biphenylyl)propionic acid | 1 |

It will be appreciated that, since the compounds of general formula I possess an asymmetric carbon atom, they are ordinarily present in the form of a racemic mixture. The resolution of such racemates may be carried out by any conventional method and the separated optically active stereo-isomers form part of the present invention.

The compounds of the invention may be made by a wide variety of methods, listed below. As the methods are, in themselves, either already known or readily apparent to those skilled in the art for making similar compounds the descriptions have been kept brief. Where the starting materials for the methods are not already known compounds, methods for their preparation will be apparent to those skilled in the art and, further, typical methods for the preparation of starting materials are given in some of the examples. In the following description for the preparation of the acids and the various acid derivatives the symbol $R_o$ has been used to represent

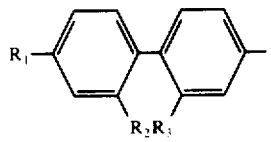

wherein $R_1$, $R_2$ and $R_3$ have the same meanings as hereinbefore.

Acids

1. Hydrolysis of

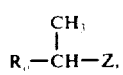

wherein Z is cyano, carbamoyl, N,N-disubstituted thiocarbamoyl, or COOR$_4$ in which R$_4$ is an ester-forming group, especially lower alkyl. The N,N-disubstituted thiocarbamoyl group is preferably derived from morpholine.

The hydrolysis may be carried out according to methods well known in the art, for example by the use of acid or alkali in water, in an organic liquid reaction medium, or in a mixture thereof; a treatment temperature of 15°-150° C. is convenient. Preferably the hydrolysis is carried out by refluxing in the presence of an alkali metal hydroxide or of a mineral acid, and the organic liquid reaction medium is a lower alkanol.

The starting materials may be prepared, for example, from the substituted acetophenones $R_o$—CO—CH$_3$ by conventional means; other methods include the methods outlined below under the "Esters" and "Amides" headings.

2. Decarboxylation of

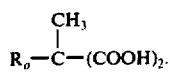

This may be carried out by heating the compound at about 200° C.

The starting materials may be conveniently prepared in conventional manner, for example by reacting an alkyl ester of an acid $R_o$—CH$_2$—COOH with an alkyl carbonate and an alkali metal alkoxide to yield an alkali metal derivative of a compound of formula $R_o$—CH—(COOalkyl)$_2$, methylating this and hydrolysing the product.

3. Methylation of $R_o$—CH$_2$—COOH.

A metal (e.g. sodium) derivatives of the acetic acid is used, prepared for example by reaction of the acid with an alkali metal amide (e.g. sodamide) in a suitable medium e.g. liquid ammonia. Conventional methylating agents may be used e.g. methyl iodide, dimethyl sulphate, and the like.

4. Oxidation of

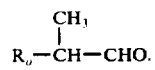

The oxidation may be carried out using any suitable oxidising agent such as permanganates, chromic acid, dichromates, per acids, hydrogen peroxide, nitric acid, hypochlorites, silver oxide, or oxygen. A very convenient procedure involves oxidation in aqueous ethanol with alkali (e.g. an alkali metal hydroxide) and silver oxide.

The starting materials may be prepared by the methods described for related compounds in our British patent specification No. 1,160,725.

5. Reductive cleavage of

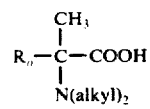

This may be achieved by conventional methods such as by catalytic hydrogenation e.g. using a palladium charcoal catalyst, or by treatment with sodium in liquid ammonia.

The starting materials may be prepared by the methods described for related compounds in our British patent specification No. 1,167,192.

6. Hydrogenation of

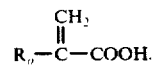

Typical procedures include hydrogenation over a conventional catalyst such as, for example, palladium, palladium oxide or platinum in an inert solvent such as a lower alkanol, benzene, toluene, xylene, tetrahydrofuran, dioxan and acetic acid, at a temperature of about 0° C. up to the reflux temperature of the system.

The starting materials may be prepared conventionally such as for example, by the following reaction scheme:

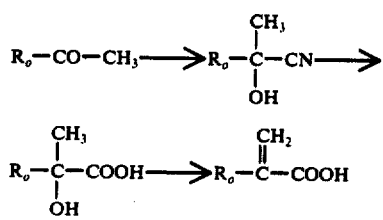

7. The reaction

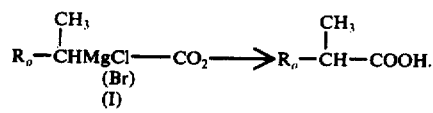

The Grignard reagent may be prepared conventionally by reaction of the appropriately substituted alkyl halide with magnesium in the presence of ether; it is then treated in ethereal solution with carbon dioxide and the additive compound so formed is decomposed with acid e.g. dilute sulphuric acid.

8. By means of the Ullmann reaction: i.e.

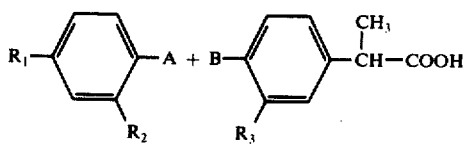

wherein A and B are halogen. Preferably A is iodine and B is bromine.

This reaction is normally carried out by heating the compounds together at 100°-350° C. in the presence of a metal catalyst especially copper powder or copper bronze.

9. Hydrolysis of

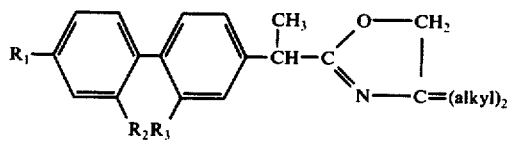

wherein "alkyl" is preferably methyl. Typical hydrolysis conditions are described under method (1).

The starting materials may be prepared using procedures similar to those described by Meyers and Temple, J. Amer. chem. Soc. 1970, 92, 6644.

10. Removal of sulphur dioxide from a compound of formula

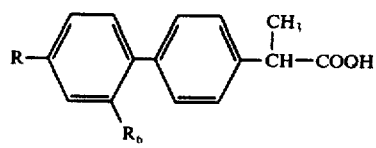

in which at least one of the symbols $R_5$, $R_6$ and $R_7$ is a fluorosulphonyl or chlorosulphonyl group and the remaining symbols correspond to the desired values of $R_1$, $R_2$ or $R_3$, by heating in the presence of a compound useful in decomposing sulphonyl fluorides and chlorides. Typical compounds are nickel, platinum, palladium, ruthenium, tris(triphenylphosphine)rhodium chloride, tris(triphenylphosphine)ruthenium dichloride, tetra(triphenylphosphine)ruthenium dichloride and tris(triphenylphosphine)rhodium fluoride. A temperature of 100°-300° C. is generally used. The reaction may be carried out in the presence of an inert organic solvent, such as benzene or xylene, although the use of a solvent is not necessary.

11. Reaction of a compound of formula

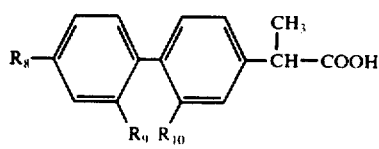

in which at least one of the symbols $R_8$, $R_9$ and $R_{10}$ is an amino group and the other symbols correspond to the desired values of $R_1$, $R_2$ or $R_3$ in known manner so as to convert said amino group to the desired halogen atom. Examples of known procedures include the Sandmeyer reaction, wherein the amino compound is diazotised and reacted with a cuprous halide, and the Schiemann reaction wherein the amino compound is diazotised in the presence of a fluoroinating agent to form a fluorodiazonium derivative which is then decomposed by heating to give the corresponding fluoro compound. Suitable fluorinating agents include hydrogen fluoride, fluoboric acid, fluosilicic acid and hexafluorophosphoric acid.

Esters

1. Esterification of the acids by conventional means:

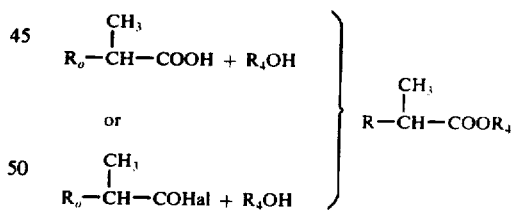

2. Alcoholysis of

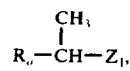

wherein $Z_1$ is cyano, carbamoyl, or N,N-disubstituted thiocarbamoyl (e.g. derived from morpholine).

3. By means of methods (3), (6), (8), (10) and (11) as described under "Acids" but starting with the desired ester in place of the acid.

4. By alcoholysis of the oxazolines described under "Acids (9)". $R_4$ is preferably a lower alkyl radical, for example alkyl containing 1 to 4 carbon atoms, most preferably methyl or ethyl, but any suitable esterifying radical may be used.

Amides

Preparation of the amides by conventional means, e.g.

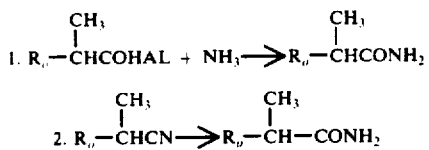

3. By means of methods (3), (6), (10) or (11) as described under "Acids" but starting with the amide in place of the acid.

Salts

1. Reaction of the acids with organic or inorganic bases.

2. Alkaline hydrolysis of

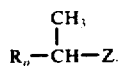

Typical inorganic salts that may be formed are the sodium and poassium salts. Typical organic salts that may be formed are amine salts, including hydroxy amine salts. For example salts with triethylamine of diethylaminoethanol or benzylamine may be formed.

Alcohols

1. Reduction of the acids or, preferably, the esters (especially alkyl esters). The use of lithium aluminum hydride in a suitable solvent e.g. ether, followed by acidification, is one example. Alternatively hydrogenation in the presence of a copper/chromium oxide catalyst may be used. Esters may be reduced with sodium in a lower alkanol.

2. By means of methods (8), (10), or (11) as described under "Acids" but starting with a protected alcohol in place of the acid. The alcohol may be protected by a conventional readily removable group e.g. benzyl, which is finally removed after the earlier synthesis stages.

Hydroxamic Acids

Preparation by conventional means: e.g

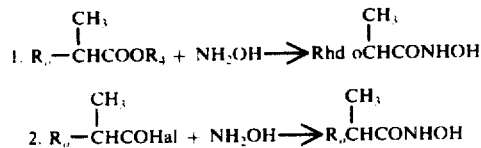

Another aspect of the invention relates to novel substituted acetic acids, and derivatives thereof, that have valuable biological properties, in particular anti-inflammatory properties.

It is now well known that certain substituted acetic acids are valuable anti-inflammatory agents. For example 4-isobutylphenylacetic acid has been used as an anti-inflammatory agent and also is effective as an analgesic and anti-pyretic compound. More recently it has been proposed to use substituted biphenylylacetic acids for rather similar purposes. For example a number of such compounds are disclosed generically, and some are named specifically, in British patent specification No. 1,091,403.

The known activity of the known substituted biphenylylacetic acids has been a short term activity in the sense that after administration the compound remains in the bloodstream, and therefore available to exert a therapeutic effect, for only a very short time, for example a few hours, for example 3 to 6 hours at the most. Accordingly if the compounds are to be used for treating chronic conditions it is considerred necessary to administer them several times a day.

Our object has been to produce novel compounds having particularly desirable long lasting anit-inflammatory activity, to produce pharamaceutical compositions of such compounds and processes for the production of such compounds and methods of treating conditions of prolonged inflammation.

Novel compounds according to this second aspect of the invention have general formula II

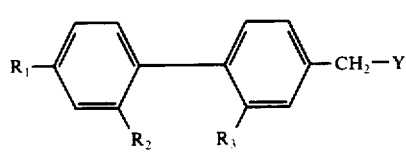

in which $R_1$, $R_2$ and $R_3$ are individually selected from fluorine, chlorine and bromine, Y is COOH, $CONH_2$, $CH_2OH$ or CONHOH together with pharmaceutically acceptable esters (i.e. compounds wherein Y is $COOR_4$ in which $R_4$ is an esterifying radical), and pharmaceutically acceptable salts of those compounds wherein Y is COOH or CONHOH.

All the compounds of the invention have long acting activity. Naturally the degree of activity exerted by any particular compound and the duration of activity will vary from compound to compound, depending upon the substituents $R_1$, $R_2$ and $R_3$ and may also vary depending upon the value of Y.

The preferred compounds are those wherein Y is COOH. It is believed that when salts, esters, amides or alcohols and hydroxamic acids are used in place of the acids the derivatives are metabolished by the animal body and are converted in the body into the corresponding acids.

Preferred compounds of the invention have at least one of $R_1$, $R_2$ and $R_3$ representing fluorine, and most preferably they have at least two of the radicals $R_1$, $R_2$ and $R_3$ representing fluorine with the other radical representing fluorine or chlorine. Accordingly the most preferred compounds are the difluoromonochloro compounds and the trifluoro compound, the latter being particularly advantageous. Thus the preferred compounds are 2,2',4'-trifluoro4-biphenylylacetic acid, 4'chloro-2,2'-difluoro-4-biphenylylacetic acid, 2'-chloro-2,4'-difluoro-4-biphenylylacetic acid and 2-chloro-2',4α-difluoro-4-biphenylylacetic acid, as well as the various derivatives of these acids wherein the carboxyl group is replaced by one of the other values of Y listed above and the salts of these acids and of the hydroxamic acids.

In addition to having long acting activity as anti-inflammatory agents, much longer for example than 2-(2-isobutylphenyl)acetic acid and 2-(2-fluoro-4-biphenylyl) acetic acid, the compounds of the invention also possess analgesic and antipyretic properties.

As with the propionic acids of the invention the half-life of the compounds of the invention in the blood of the subject to which they are administered is a good indication of their duration of activity. The half-life may ve measured by giving oral doses of the compounds and determining levels in the plasma at various times thereafer, as previously described. As with the propionic acids of the invention one of the best methods of indicating long acting anti-inflammatory activity of the compounds is by means of a test in which compounds are administered chronically e.g. the rat adjuvant arthritis test.

Thus, for example in this test, one of the preferred compounds, 2,2', 4'-trifluoro-4-biphenylacetic acid was found to be more than 30 times as active as 2-fluoro-4-biphenylylacetic acid which is used as the standard of reference in the test when comparing with other biphenylylactic acids.

The acetic acids of the invention may be made by a wide variety of methods listed below. As the methods are, in themselves, either known of readily apparent to those skilled in the art for making similar compounds the descriptions have been kept brief. Where the starting materials for the methods are not already known compounds, methods for their preparation will be apparent to those skilled in the art and, further, typical methods for the preparation of starting materials are given in some of the examples. In the following description for the preparation of the acids and the various acid derivatives the symbols $R_o$ has been used to represent

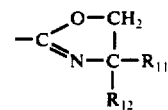

wherein $R_1$, $R_2$ and $R_3$ have the same meaning as hereinbefore.

Acids

1. Hydrolysis of $R_o$ — $CH_2$— Z, wherein Z is cyano; carbamoyl; N,N-disubstituted thiocarbamoyl;

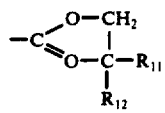

in which $R_{11}$ and $R_{12}$ are the same or different and are alkyl e.g. methyl, or aryl or together with the carbon atom to which they are bonded form a carbocyclic ring; or $COOR_4$ in which $R_4$ is an ester-forming group, especially lower alkyl. The N,N-disubstituted thiocarbamoyl group is preferably derived from morpholine.

The hydrolysis may be carried out according to methods well known in the art, for example by the use of acid or alkali in water, in an organic liquid reaction medium, or in a mixture thereof; a treatment temperature of 15°–150° C. is convenient. Preferably the hydrolysis is carried out by refluxing in the presence of an alkali metal hydroxide or of a mineral acid, and the organic liquid reaction medium is a lower alkanol.

The starting materials may be prepared by conventional means. Thus, compounds in which Z is $COOR_4$ may be obtained for example a. by means of the Arndt-Eistert reaction in which $R_oCOCl$ is reacted with diazomethane to give a diazoketone which is then treated with silver oxide and methanol b. by reducing $R_oCO\ COOR_4$ or c. by the methods outlined below under the "Esters" heading.

Compounds in which Z is cyano may be obtained, for example by treating $R_oCH_2$.Halide with an alkali metal cyanide.

Compounds in which Z is

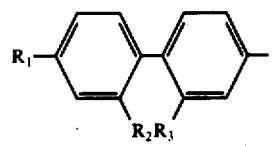

may be obtained, for example, by the methods described for related compounds in our U.K. Application No. 39939/71 (OLS 2241913).

Compounds in which Z is N,N-disubstituted thiocarbamoyl may be obtained for example by the Willgerodt reaction in which $R_oCO$—$CH_3$ is reacted with sulphur and a secondary amine, e.g. morpholine, at a temperature of, for example from 50° to 200° C., preferably under reflux.

The carbamoyl derivatives may be obtained by conventional means e.g. from $R_oCOCH_3$ or $R_oCH_2$—CHO, or by the methods outlined below under the "Amides" heading.

2. Oxidation of $R_oCH_2Q$, wherein Q is CHO or $CH_2OH$.

The oxidation may be carried out using any suitable oxidising agent such as permanganates, chromic acid, dichromates, peracids, hydrogen peroxide, nitric acid, hypochlorities, silver oxide or oxygen. A very convenient procedure involves oxidation in aqueous ethanol with alkali (e.g. an alkali metal hydroxide) and silver oxide.

The alcohol may be prepared, for example by reacting $R_oMg$ Halide with ethylene oxide.

3. The reaction $R_oCH_2Mg.Halide + CO_2 \rightarrow R_oCH_2.COOH$

The Grignard reagent may be prepared conventionally by reaction of the appropriately substituted alkyl halide with magnesium in the presence of e.g. an ester; it is then treated in ethereal solution with carbon dioxide and the addition compound so formed is decomposed with acid e.g. sulphuric acid.

4. By means of the Ullmann reaction: i.e.

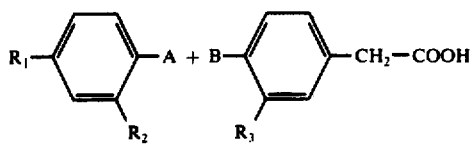

wherein A and B are halogen. Preferably A is iodine and B is bromine.

This reaction is normally carried out by heating the compounds together at 100°–350° C. in the presence of a metal catalyst especially copper powder or copper bronze.

5. Removal of sulphur dioxide from a compound of formula

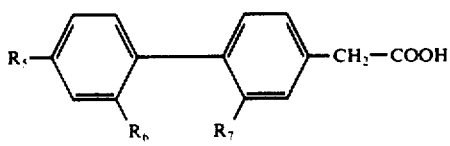

in which at least one of the symbols $R_5$, $R_6$ and $R_7$ is a fluorosulphonyl or chlorosulphonyl group and the remaining symbols correspond to the desired values of $R_1$, $R_2$ or $R_3$, by heating in the presence of a compound useful in decomposing sulphonyl fluorides and chlorides. Typical compounds are nickel, platinum, palladium, ruthenium, tris (triphenylphosphine) rhodium chloride, tri(triphenylphosphine) ruthenium dichloride, tetra(triphenylphosphine) ruthenium dichloride and tris(triphenylphosphine) rhodium fluoride. A temperature of 100°–300° C. is generally used. The reaction may be carried out in the presence of an inert organic solvent, such as benzene or xylene, although the use of a solvent is not necessary.

6. Reaction of a compound of formula

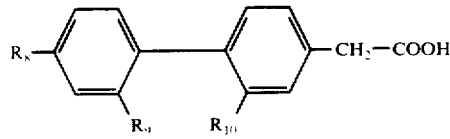

in which at least one of the symbols $R_8$, $R_9$ and $R_{10}$ is an amino group and the other symbols correspond to the desired values of $R_1$, $R_2$ or $R_3$ in known manner so as to convert said amino group to the desired halogen atom. Examples of known procedures include the Sandmeyer reaction, wherein the amino compound is diazotised and reacted with a cuprous halide, and the Schiemann reaction wherein the amino compound is diazotised in the presence of a fluorinating agent to form a fluorodiazonium derivative which is then decomposed by heating to give the corresponding fluoro compound. Suitable fluorinating agents include hydrogen fluoride, fluoboric acid, fluosilicic acid and hexafluorophosphoric acid.

7. Hydrogenolysis of $R_oCHOH.COOH$

This may be achieved by conventional methods, for example catalytic hydrogenation using e.g. a palladium charcoal catalyst, or by treatment with phosphorus and iodine.

The starting materials may be prepared by reacting $R_oCHO$ with HCN and hydrolysing the product. hydrolysing 8. By means of Erlenmeyer's azlactone synthesis, in which $R_oCHO$ is condensed with an acylglycine, e.g. $C_6H_5.CO.NH.CH_2CO.OH$, in the presence of acetic anhydride, hydrolysing the azlactone and oxidizing e.g. with hydrogen peroxide, the substituted pyruvic acid so obtained.

Esters

1. Esterification of the acids by conventional means:

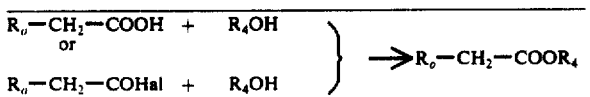

2. Alcoholysis of $R_oCH_2—Z_1$, wherein $Z_1$ is cyano, carbamoyl, N,N-disubstituted thiocarbamoyl or

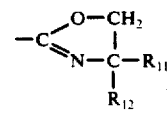

3. By means of methods 4, 5 and 6 as described under "Acids" but starting with the desired ester in place of the acid.

4. By means described in method 1 under "Acids" for obtaining compounds in which Z is $COOR_4$. $R_4$ is preferably a lower alkyl radical, for example alkyl containing 1 to 4 carbon atoms, most preferably methyl or ethyl, but any suitable esterifying radical may be used.

Amides

Preparation of the amides by conventional means, e.g.:
1. $R_o—CH_2COHal + NH_3 \rightarrow R_oCH_2CONH_2$
2. $R_o—CH_2CN \rightarrow R_o—CH_2—CONH_2$
3. By means of methods 5 or 6 as described under "Acids" but starting with the amide in place of the acid.

Salts

1. Reaction of the acids with organic or inorganic bases.
2. Alkaline hydrolysis of $R_o—CH_2—Z$.

Typical inorganic salts that may be formed are the sodium and potassium salts. Typical organic salts that may be formed are amine salts, including hydroxy amine salts. For example salts with triethylamine or diethylaminoethanol or benzylamine may be formed.

Alcohols

1. Reduction of the acids or, preferably, the esters (especially alkyl esters). The use of lithium aluminium hydride in a suitable solvent e.g. ether, followed by acidification, is one example. Alternatively hydrogenation in the presence of a copper/chromium oxide catalyst may be used. Esters may be reduced with sodium in a lower alkanol.

2. By means of methods 4, 5 or 6 as described under "Acids" but starting with a protected alcohol in place of the acid. The alcohol may be protected by a conventional readily removable group e.g. benzyl, which is finally removed after the earlier synthesis stages.

3. By means described in method 2 under "Acids".

Hydroxamic Acids

Preparation by conventional means: e.g.
1. $R_o—CH_2.COOR_4 + NH_2OH \rightarrow R_oCH_2.CO.NHOH$
2. $R_o—CH_2.CO.Hal + NH_2OH \rightarrow R_oCH_2.CO.NHOH$ Methods of treating inflammatory conditions according to the invention comprise administering to the living animal body, for example, a human patient, one of the compounds of the invention in a pharmaceutically acceptable and effective dosage, administration preferably being oral. Methods of the invention also comprise the treatment of conditions of pain or pyretic conditions individually or in combination or in any combination with inflammatory conditions by similar administration of a compound of the invention. The compounds may be administered in conventional manner for other anti-inflammatory agents, for example orally, rectally, topically or parenterally, preferably orally or rectally. The optimum dosage rate varies with the route of administration, but normally lies within the range 0.014–14.0 mg./kg.day, more usually between 0.035–3.5 mg./kg./day. The unit dose may vary from 0.5 mg. to 500 mg. preferably 1 to 100 mg. For oral administration the dosage rate is usually 0.5–500 mg, and preferably 1 to 100 mg, per subject per day. Preferably dosage is required not more than once, or at the most twice a day, for as long as is required.

For ease of administration the compounds are preferably formulated as therapeutic compositions which comprise a compound of the invention in associated with pharmaceutical excipients for the production of compositions for oral, rectal, topical or parenteral administration. These compositions preferably contain 0.1–90% by weight of a compound of the invention.

Preferred compositions of the invention are compositions for oral administration, and these are the conventional pharmaceutical forms for such administration, such as for example tablets, capsules, lozenges, powders, effervescent granules, syrups and aqueous and oily suspensions. The excipients used in the preparation of these compositions are the excipients of the pharmacist's art. Thus in the preparation of tablets, typical excipients include disintegrating agents, e.g., maize starch and lubricating agents, e.g., magnesium stearate. In the preparation of capsules, standard gelatin capsules may be used containing the active ingredient alone or admixed with a diluent. The liquid compositions may comprise as excipients water and sucrose to provide syrups, water, dispersing agents and suspending agents, e.g., sodium carboxymethylcellulose to provide aqueous suspensions, and a non-toxic oil, e.g., a vegetable oil such as arachis oil and a suspending agent to provide oily suspensions.

Other preferred compositions of the invention are compositions for rectal administration, and these are the conventional pharmaceutical forms for such administration, such as for example suppositories with fatty glyceride or polyethylene glycol bases.

Compositions for topical use are the conventional pharmaceutical forms for such application, such as ointments, creams and lotions. Ointments and creams may be water miscible or water-immiscible in character and include emulsions prepared from emulsifying waxes and oils and those prepared from water miscible polyethylene glycols. Lotions may comprise a solution in an aliphatic alcohol with 1–4 carbon atoms which may contain a small proportion of water.

Compositions for parenteral administration are the conventional pharmaceutical forms for such administrations, for example sterile suspensions in aqueous or oily media or sterile solutions in propylene glycol.

In some formulations it may be beneficial to use the compounds of the invention in the form of particles of very small size, such as for example as obtained by fluid energy milling, e.g. micronizing.

The products of the present invention may of course be employed in combination with other active anti-inflammatory agents, analgesics, and antipyretic agents, or with other drugs.

The biphenylylacetic acids of the invention have other valuable properties. For example, they possess fibrinolytic and thrombolytic activity and also inhibit platelet aggregation induced by various agents such as adrenaline.

The fibrinolytic activity is assessed by the euglobulin lysis time test described by Van Kaulla in Chemistry of Thrombosis: Human Fibrinolytic Enzyme, 1963, p79, published by Charles C. Thomas, Springfield, Illinois.

The thrombolytic activity is assessed by the hanging clot test described by Van Kaulla, J. Med. Chem. 1965, 8, 164.

The effect on platelet aggregation is assessed by the test of Born; Nature, 1962, 194,927.

Drugs possessing such properties are useful in the treatment and/or prophylaxis of various thrombotic disorders. When being used in such treatment or prophylaxis they may be formulated and administered in a manner similar to that when being used as anti-inflammatory agents, as described previously.

The biphenylylacetic acids of the invention also have the property of inhibiting mammalian neoplastic metastasis i.e. the process whereby neoplastic cells migrate from the region of the primary neoplasm to another region of the body where they locate and develop to form secondary neoplasms. These compounds also ameliorate the pain associated with such neosplasms.

The ability to inhibit neoplastic metastisis in mammals is known in the art as antimetastatic activity. The antimetastatic activity is demonstrated by experiments in rats. In these experiments one group of rats (group A) is given a daily oral dose of the compound under test for a few days. This group of rats and a control group of rats (group B) which have received no test compound are then injected intravenously with neoplastic cells of a type that are known to produce pulmonary neoplasms in rats. Daily oral administration of the test compound to the rats in group A is continued for several weeks. The rats in each group are then killed and their lungs examined. A significant reduction in pulmonary neoplasms (seen as nodules in the lungs) in the rats of group A compared with the control group B demonstrates the antimetastatic activity of the test compound.

When being used to inhibit mammalian neoplastic metastasis the biphenylylacetic acid may be formulated and administered in a manner similar to that when being used as anti-inflammatory agents, except that dosage rates are generally higher e.g. 0.1–100 mg./kg./day, more usually 0.1–50 mg./kg./day and especially 0.5–25 mg./kg./day, given in single or divided doses. A daily dosage for an adult human is generally within the range 0.01–3.5g., especially 0.035–1.75g.

The following are some non-limitative Examples of the preparation of starting materials, the preparation of the compounds of the invention, and compositions of the invention.

EXAMPLE 1

2,4-Difluoroiodobenzene and 4-bromo-3-nitroacetophenone were reacted under Ullmann conditions to give 4-acetyl-2',4'-difluoro-2-nitrobiphenyl, b.p. 150°–158° C./0.2 mm., and this was reduced with stannous chloride to give 4-acetyl-2-amino-2',4'-difluorobiphenyl, m.p. 93°–95° C. By similar methods there were obtained 4-acetyl-2'-chloro-4'-fluoro-2-nitrobiphenyl, b.p. 178°–190°/0.2 mm m.p. 62°–64° C. and 4-acetyl-2-amino-2'-chloro-4'-fluorobiphenyl, m.p. 84°–86° C; 4-acetyl-4'-chloro-2'-fluoro-2-nitrobiphenyl, b.p. 174°–180°/0.2 mm., m.p. 85°–86° C. and 4-acetyl-2-amino-2'-fluoro-4'-chlorobiphenyl, m.p. 115° C; 4-acetyl-2',4'-dichloro-2-nitrobiphenyl, m.p. 72°–74° C. and 4-acetyl-2-amino-2',4'-dichlorobiphenyl, m.p. 75°–76° C; 4-acetyl-2',4'-dibromo-2-nitrobiphenyl, b.p. 210° C./0.3 mm. and 4-acetyl-2-amino-2',4'-dibromobiphenyl, m.p. 107°–109° C; 4-acetyl-4'-bromo-2'-fluoro-2-nitrobiphenyl, m.p. 116°–117° C. and 4-acetyl-2-amino-4'-bromo-2'-fluorobiphenyl, m.p. 120°–121° C; 4-acetyl-2'-bromo-4'-fluoro-2-nitrobiphenyl, b.p. 188°–200° C./0.3 mm., m.p. 75°–77° C. and 4-acetyl-2-amino-2'-bromo-4'-fluorobiphenyl, m.p. 98°–100° C; 4-acetyl-4'-bromo-2'-chloro-2-nitrobiphenyl, b.p. 185°–190° C./0.2 mm. and 4-acetyl-2-amino-4'-bromo-2'-chlorobiphenyl, m.p. 93°–95° C; and 4-acetyl-2'-bromo-4'-chloro-2-nitrobiphenyl, m.p. 84°–86° C; and 4-acetyl-2-amino-2'-bromo-4'-chlorobiphenyl, m.p. 98°–100° C.

EXAMPLE 2

4-Acetyl-2-amino-2',4'-difluorobiphenyl prepared as described in Example 1 was subjected to the Schiemann reaction using fluoboric acid to give 4-acetyl-2,2',4'-trifluorobiphenyl, m.p. 92°–94° C. By a similar method, starting from the appropriate products of Example 1, there were obtained 4-acetyl-4'-chloro-2,2'-difluorobiphenyl, m.p. 69°–70° C. and 4-acetyl-4'-bromo-2,2'-difluorobiphenyl, m.p. 75°–76° C.

EXAMPLE 3

4-Acetyl-2-amino-2',4'-difluorobiphenyl from Example 1 was subjected to the Sandmeyer reaction using cuprous chloride to give 4-acetyl-2-chloro-2',4'-difluorobiphenyl, b.p. 132°–134° C./0.3 mm. By a similar method there were obtained from the appropriate starting material 4-acetyl-2,2-dichloro-4-fluorobiphenyl, 4-acetyl-2,4'-dichloro-2'-fluorobiphenyl, b.p. 134°–138° C./0.05 mm; 4-acetyl-2,2',4'-trichlorobiphenyl, b.p. 154°–155° C./0.2 mm; 4-acetyl-2',4'-dibromo-2-chlorobiphenyl, b.p. 174°–178° C./0.5 mm; 4-acetyl-4'-bromo-2-chloro-2'-fluorobiphenyl, b.p. 165°–170° C./0.1 mm; 4-acetyl-2'-bromo-2-chloro-4'-fluorobiphenyl, b.p. 168°–170° C./1.0 mm; and, using cuprous bromide instead of cuprous chloride in the Sandmeyer reaction, 4-acetyl-2,2'-4'-tribromobiphenyl, m.p. 73°–75.5° C; 4acetyl-2,4'-dibromo-2'-fluorobiphenyl, m.p. 63°–64° C; 4-acetyl-2,2'-dibromo-4'-fluorobiphenyl, b.p. 166°–168° C./0.8 mm; 4-acetyl-2,4'-dibromo-2'-chlorobiphenyl, m.p. 53°–54° C. and 4-acetyl-2,2'-dibromo-4'-chlorobiphenyl, m.p. 75°–77° 77° C.

EXAMPLE 4

2,4-Dichloroiodobenzene and 2,5-dibromonitrobenzene were reacted under Ullmann conditions to give 4-bromo-2',4'-dichloro-2-nitrobiphenyl, m.p. 112°–115° C. This was reduced with stannous chloride to give 2-amino-4-bromo-2',4'-dichlorobiphenyl, b.p. 170°–175° C./0.2 mm. This was subjected to the Schiemann reaction using fluoboric acid to give 4-bromo-2',4'-dichloro-2-fluorobiphenyl, m.p. 63°–65° C. This was reacted with cuprous cyanide in dimethyl formamide to give 2',4'-dichloro-4-cyano-2-fluorobiphenyl, m.p. 98°–103° C. which was then reacted with methylmagnesium iodide followed by hydrolysis with dilute hydrochloric acid to yield 4-acetyl-2',4'-dihloro-2-fluorobiphenyl, m.p. 65°–67° C.

EXAMPLE 5

4-Acetyl-2-amino-2'-chloro-4'-fluorobiphenyl, obtained from Example 1 was subjected to diazotisation in hydrofluoric acid with sodium nitrate to give 4-acetyl-2'-chloro-2,4'-difluorobiphenyl, b.p. 140°–160° C./1 mm. By a similar method, using the appropriate starting materials from Example 1, there were obtained 4-acetyl-2',4'-dibromo-2-fluorobiphenyl; 4-acetyl-2'-bromo-2,4'-difluorobiphenyl; 4-acetyl-4'-bromo-2'-chloro-2-fluorobiphenyl and 4-acetyl-2'-bromo-4'-chloro-2-fluorobiphenyl.

EXAMPLE 6

4-Acetyl-2,2',4'-trifluorobiphenyl from Example 2 was treated with sodium isopropoxide and ethyl chloroacetate according to the Darzens reaction to give a mixture of esters containing the crude isopropyl ester of 3-(2,2',4'-trifluorobiphenylyl)2,3-epoxybutyric acid, which was hydrolysed with sodium hydroxide/aqueous alcohol to give a crude sodium salt of the said butyric acid. This was decarboxylated by heating at 90° C. to give 2-(2,2',4'-trifluoro-4-biphenylyl)propionaldehyde, b.p. 132°–134° C./1 mm. Each of the other 4-acetyl-trihalobiphenyls produced in Examples 2 to 5 was subjected to the same process to produce the corresponding trihalo aldehydes. Such aldehydes included, inter alia, 2-(4'-chloro-2,2'-difluoro-4-biphenylyl)propionaldehyde, b.p. 174°–180° C./0.1 mm; 2-(2,4'-dichloro-2'-fluoro-4-biphenylyl)propionaldehyde, b.p. 152°–156° C./0.1 mm; 2-(2',4'-dichloro-2-fluoro-4-biphenylyl)propionaldehyde, b.p. 160°–162° C./0.3 mm; 2-(2,2',4'-trichloro-4-biphenylyl)propionaldehyde, b.p. 190°–192° C./1.0 mm; 2-(2,4'-dibromo-2'-fluoro-4-biphenylyl)propionaldehyde, b.p. 167°–170° C./0.1 mm; 2-(4'-bromo-2,2'-difluoro-4-biphenylyl)propionaldehyde, b.p. 145°–146° C./0.07 mm; 2-(4'-bromo-2-chloro-2'-fluoro-4-biphenylyl)propionaldehyde, b.p. 155°–160° C./0.07 mm. and 2-(2-bromo-4'-chloro-2'-fluoro-4-biphenylyl)propionaldehyde, b.p. 158°–160° C./0.07 mm.

EXAMPLE 7

Hydroxylamine sulphate (3.02 g.) was added to an aqueous solution of sodium acetate [prepared from glacial acetic acid (2.4 ml.), 18N aqueous sodium hydroxide (2.34 ml.) and water (23 ml.)]. 2-(2,2',4'-Trifluoro-4-biphenylyl)propionaldehyde (8.26 g.) in ethanol (23 ml.) was added and the mixture was stirred at room temperature for 2.5 hours and then at 90° C. for 1 minute. After cooling, the precipitated oxime was suspended in water containing nickel sulphate (0.2 g.) and heated to reflux to obtain an aqueous suspension of 2-(2,2',4'-trifluoro-4-biphenylyl)propionamide. Aqueous sodium hydroxide (18N, 6.75 ml.) was then added and refluxing continued for 24 hours. The resulting solution was cooled to 40° C., acidified with concentrated hydrochloric acid, and the product isolated in ether. After some purification by a conventional back-extraction technique with aqueous potassium carbonate, the final ether extract was evaporated to dryness. This crude acid in methylene chloride was chromatographed on a column of a synthetic magnesia/silica gel adsorbent. Evaporation of the eluate and recrystallisation of the residue from petroleum ether (b.p. 80°–100° C.) gave 2-(2,2',4'-trifluoro-4-biphenylyl)propionic acid, m.p. 105°–108° C.

By a similar method there were obtained from the appropriate aldehydes of Example 6 the corresponding propionic acids. The physical data for the various compounds obtained are set out in the following Table wherein the symbols $R_1$, $R_2$ and $R_3$ designate the substituents in formula I and the figure in the right-hand column is the melting point of the resultant acid.

| $R_1$ | $R_2$ | $R_3$ | m.p. (° C.) |
|---|---|---|---|
| F | F | Cl | 91–93 |
| F | Cl | F | 104 |
| F | Cl | Cl | 111–114 |
| Cl | F | F | 95–6 |
| Cl | F | Cl | 126–7 |
| Cl | Cl | F | 96–99 |
| Cl | Cl | Cl | 90–92 |
| Br | Br | Br | Glass |
| Br | Br | F | Glass |
| Br | Br | Cl | Glass |
| Br | F | Br | 127–128 |
| Br | F | F | 127 |
| Br | F | Cl | 129–130 |
| F | Br | Br | Glass |
| F | Br | F | 87–89 |
| F | Br | Cl | 91–94 |
| Br | Cl | Br | Glass (Benzylamine salt 126–8) |
| Br | Cl | F | 109–112 |
| Cl | Br | Br | Glass (Benzylamine salt 118–121) |
| Cl | Br | F | 90–92 |
| F | Cl | Br | Glass |
| Cl | F | Br | 119–120 |
| F | F | Br | 112–113.5 |

EXAMPLE 8

Benzylamine (0.15 ml.) was added to an ethereal solution of 2-(2,2',4'-trifluoro-4-biphenylyl)propionic acid (280 mg. in 20 ml.). The mixture was stirred at room temperature for 15 minutes and the salt was then collected, washed with ether and recrystallised from a mixture of acetone and light petroleum (b.p. 40°–60° C.). The product was benzylammonium 2-(2,2',4'-trifluoro-4-biphenylyl)propionate m.p. 133°–134° C.

By the same method, starting from the appropriate acid, there was obtained benzylammonium 2-(2',4'-dichloro-2-fluoro-4-biphenylyl)propionate, m.p. 111°–113° C. By the same method are obtained other organic salts.

EXAMPLE 9

A solution of sodium hydroxide (0.1 g.) in water (1.0 ml.) was added to a solution of 2-(2,2',4'-trifluoro-4-biphenylyl)propionic acid (0.5 g.) in acetone (5 ml.). After stirring for 15 minutes the resultant salt was filtered, washed with acetone and recrystallised from water. The resultant sodium 2-(2,2',4'-trifluoro-4-biphenylyl)propionate had m.p. 222°–224° C. By the same method are obtained other inorganic, especially sodium, salts.

EXAMPLE 10

A mixture of 2-(2,2', 4'-trifluoro-4-biphenylyl) propionic acid (2.0 g.), absolute ethanol (25 ml.), and concentrated $H_2SO_4$ (1 ml.) was refluxed overnight. The solution was cooled, diluted with water and the ester isolated in ether. Distillation gave a colourless oil b.p. 124°–126°/0.3 mm. which solidified and was then crystallised from light petroleum (b.p. 40°–60° C.) giving colourless needles of ethyl 2-(2,2',4'-trifluoro-4-biphenylyl)propionate m.p. 36°–38° C.

In the same manner there was obtained ethyl 2-(4'-bromo-2,2'-difluoro-4-biphenylyl)propionate, b.p. 152°–153° C./0.1 mm. By the same method there are obtained other lower alkanoate esters, especially those wherein the alkyl contains 1 to 4 carbon atoms, from acids produced in Example 7.

EXAMPLE 11

Ethyl 2-(2,2',4'-trifluoro-4-biphenylyl)propionate (708 mg.) (Example 10) in ethanol (5 ml.) and water (5 ml.) containing sodium hydroxide (0.4 ml. of 18N) was refluxed for 1 hour. The ethanol was distilled and the residual mixture was cooled and acidified. The solid acid was collected, washed, dried and recrystallised from light petroleum (b.p. 80°–100° C.) to form colourless needles, m.p. 107°–108.5° C.

EXAMPLE 12

A solution of ethyl 2-(2,2',4'-trifluoro-4-biphenylyl)-propionate (0.5 g.) in dry ether (10 ml.) was added over 5 minutes to a stirred suspension of lithium aluminium hydride (0.1 g.) in dry ether (10 ml.). After refluxing for 90 minutes the excess hydride was decomposed by the successive addition of moist ether, water, and finally dilute sulphuric acid.

The propanol was isolated in ether, washed, dried, evaporated and distilled giving a colourless opalescent oil, b.p. 140°–142°/0.7 mm. which solidified and was then crystallised from light petroleum (b.p. 62°–68° C.) giving colourless needles of 2-(2,2',4'-trifluoro-4-biphenylyl) propan-1-ol, m.p. 58°–59° C.

In the same way but using the appropriate starting materials, there were obtained 2-(4'-bromo-2,2'-difluoro-4-biphenylyl)propan-1-ol, b.p. 139°–140° C./0.05 mm. and 2-(2',4'-dichloro-2-fluoro-4-biphenylyl)propan-1-ol, b.p. 174°–176° C./2 mm, and other alcohols may be made by the same method from acids produced in Example 7.

EXAMPLE 13

2-(2',4'-Dichloro-2-fluoro-4-biphenylyl)propionic acid (1.2 g.) was dissolved in methanol (10 ml.) and concentrated $H_2SO_4$ (0.3 ml.) and refluxed for 5 hours. The methanol was removed and the residue diluted with water, extracted with ether, washed with aqueous potassium carbonate, water, and dried over anhydrous sodium sulphate. The ether was removed and the residue distilled in vacuo. The product was methyl 2-(2',4'-dichloro-2-fluoro-4-biphenylyl)propionate, b.p. 167°–168° C./1 mm.

EXAMPLE 14

2-(2,2',4'-Trifluoro-4-biphenylyl)propionic acid (1.0 g.) in thionyl chloride (10 ml.) was refluxed for 1 hour. Excess thionyl chloride was distilled and the residual acid chloride in ether (10 ml.) was added dropwise to ammonia (10 ml. d, 0.880), stirred and cooled in ice. After 15 minutes, a further quantity (250 ml.) of ether was added to dissolve the amide, the ether layer was washed with dilute ammonia and water, dried, and evaporated.

Recrystallisation from methylene chloride/light petroleum (b.p. 40°–60° C.) gave colourless needles of 2-(2,2',4'-trifluoro-4-biphenylyl)propionamide, m.p. 136°–137° C. Other amides may be made by the same method from the acids produced in Example 7.

EXAMPLE 15

4-Acetyl-2,2',4'-trifluorobiphenyl (Example 2) on refluxing with sulphur and morpholine according to the Willgerodt reaction followed by acid hydrolysis gave 2,2',4'-trifluoro-4-biphenylylacetic acid, m.p. 145°-147° C. Esterification by refluxing with ethanol and sulphuric acid afforded ethyl 2,2',4'-trifluoro-4-biphenylylacetate b.p. 130°-136°/0.4 mm., m.p. 50°-52° C., which after reacting with ethyl carbonate and sodium ethoxide followed by methyl sulphate gave ethyl 2-methyl-2-(2,2',4'-trifluoro-4-biphenylyl)malonate and after hydrolysis with aqueous sodium hydroxide and ethanol, 2-methyl-2-(2,2',4'-trifluoro-4-biphenylyl)malonic acid.

2-Methyl-2-(2,2',4'-trifluoro-4-biphenylyl)malonic acid (1.9 g.) was decarboxylated by heating at 180°-200° C. for 30 mins. The residual material was purified by preparative layer chromatography on Kieselgel PF$_{254}$ using the solvent mixture 5% acetic acid/light petroleum (b.p. 60°-80° C.) and eluting with ethyl acetate. The crystalline residue after removal of ethyl acetate was recrystallised from light pertroleum (b.p. 80°-100° C. to give 2-(2,2',4'-trifluoro-4-biphenylyl)propionic acid, m.p. 105°-107° C.

EXAMPLE 16

Potassium hydroxide (3.04 ml. of 13.2 N) diluted with water (7.3 ml.) was added dropwise to a stirred solution of silver nitrate (6.8 g.) in water (8 ml.). The slurry of silver oxide was diluted with ethanol (9 ml.) followed by the slow addition of a solution of 2-(2,2',4'-trifluoro-4-biphenylyl)propionaldehyde (5.1 g.) (Example 6) in ethanol (17 ml.). After stirring for 15 mins., potassium hydroxide (1.8 ml. of 13.2N) and water (1.8 ml.) were added over 1 hour, the temperature being maintained at 43°-45° C. After stirring at 40° C. for 30 mins., the silver was collected and washed with water. Ethanol was removed from the filtrate by distillation under reduced pressure, the residue acidified with dilute hydrochloric acid and the acid isolated in ether and extracted into potassium carbonate solution (2.5%). The aqueous extracts were acidified and the liberated acid isolated in ether, washed with water dried and evaporated. The residual 2-(2,2',4'-trifluoro-4-biphenylyl)propionic acid after recrystallisation from light petroleum (b.p. 80°-100° C.) had m.p. 105°-108° C.

EXAMPLE 17

2-[1-(2,2',4'-Trifluoro-4-biphenylyl)ethyl]-4,4-dimethyl-2-oxazoline (0.53 g.) was stirred and refluxed with hydrochloric acid (5 ml. of 2N) for 5 hrs. The mixture was diluted with water, extracted with ether and the latter extracted with 2.5% potassium carbonate solution. The aqueous extracts were acidified with dilute hydrochloric acid and the precipitate isolated in ether, washed with water, dried and evaporated. The residue was recrystallized from light petroleum (b.p. 80°-100° C.) to give 2-(2,2',4'-trifluoro-4-biphenylyl)propionic acid, m.p. 107°-108.5° C.

EXAMPLE 18

Potassium hydroxide (1.0 g.) in methanol (20 ml.) was added dropwise to a solution of methyl 2-(2,2',4'-trifluoro-4-biphenylyl)propionate (0.42 g.) and hydroxylamine hydrochloride (0.5 g.) in methanol (10 ml.) until the solution was just alkaline to limits. After standing overnight at room temperature the filtrate from inorganic salts was evaported to small bulk, diluted with water, washed with ether, acidified with dilute hydrochloric acid, re-extracted with ether, washed with ether, dried and evaporated to dryness. The residue was recrystallised from benzene to give 2-(2,2',4'-trifluoro-4-biphenylyl) propionhydroxamic acid, m.p. 148°-150° C. (decomp.)

Example 19

No. 5 hard gelatin capsules were prepared each containing the following:

| (a) | 2-(2,2',4'-trifluoro-4-biphenylyl)propionic acid | 5 mg. |
|---|---|---|
|   | lactose | 95 mg. |
| (b) | 2-(2,2',4'-trifluoro-4-biphenylyl)propionic acid | 5 mg. |
|   | calcium phosphate | 5 mg. |
|   | maize starch | 90 mg. |
| (c) | 2-(2,2',4'-trifluoro-4-biphenyly)propionic acid | 5 mg. |
|   | maize starch \\ lactose } equal parts by weight \\ calcium phosphate | 95 mg. |

EXAMPLE 20

The following mixture (parts by weight) was formed into tablets in conventional manner, each tablet containing 5 mg. of active ingredient:

| 2-(2',4'-trifluoro-4-biphenylyl)propionic acid | 5 |
|---|---|
| maize starch | 30 |
| lactose | 163 |
| stearic acid | 1 |
| magnesium stearate | 1 |

Compositions similar to those described in Examples 19 and 20 were prepared containing as active ingredient other compounds of the invention.

EXAMPLE 21

2,4-Difluoroidobenzene and 4-bromo-3-nitroacetophenone were reacted under Ullmann conditions to give 4-acetyl-2',4'-difluoro-2-nitrobiphenyl, b.p. 150°-158° C./0.2mm. and this was reduced with stannous chloride to give 4-acetyl-2-amino-2',4'-difluorobiphenyl, m.p. 93°-95° C. This was then subjected to the Schiemann reaction using fluoroboric acid to give 4-acetyl-2,2',4'-trifluorobiphenyl, m.p. 92°-94° C.

A mixture of 4-acetyl-2,2',4'-trifluorobiphenyl (4.4 g., 17.6 m.moles), sulphur (1 g.) and morpholine (5 ml.) was stirred under reflux for 16 hours to give the thiomorpholide. After cooling, and the addition of acetic acid (glacial, 25 ml.), concentrated sulphuric acid (4 ml.) and water (10 ml.) the mixture was stirred and refluxed for 24 hours. Ice-water was added to precipitate a crude solid. This was taken up in ether and back-extracted with aqueous potassium carbonate. The extracts were washed with ether, acidified, and re-extracted with ether. Evaporation gave 4.2 g. of crude 2,2',4'-trifluoro-4-biphenylylacetic acid. This was then mixed with absolute alcohol (65 ml.) and concentrated sulphuric acid (3 ml.) and the mixture refluxed overnight. Excess alcohol was distilled off and the residue diluted with water (100 ml.). The product was isolated with ether, washed with aqueous sodium bicarbonate, dried, evaporated and distilled (b.p. 130°-136°/0.4 mm.) to give 3.2 g. of pale yellow oil which solidified on standing. This was recrystallised from 40–60 petroleum ether to give ethyl 2,2',4'-trifluoro-4-biphenylylacetate having a m.p. of 50°-52° C.

The ester (650 mg.) was mixed with water (5 ml.), industrial methylated spirits (IMS) (5 ml.) and aqueous sodium hydroxide (0.4 ml; 18N), and refluxed for 1 hour. IMS was distilled and the residue acidified with dilute hydrochloric acid. The precipitate was filtered, washed with water, dried and recrystallised from 80–100 petroleum ether to give colourless needle clusters of 2,2',4'-trifluoro-4-biphenylylacetic acid having a m.p. of 145°–147° C.

EXAMPLE 22

4-Acetyl-2-amino-2',4'-difluorobiphenyl from Example 21 was subjected to the Sandmeyer reaction using cuprous chloride to give 4-acetyl-2-chloro-2',4'-difluorobiphenyl, b.p. 132°–134° C./0.3mm. In a similar way to that described in Example 21 this was treated with sulphur and morpholine with subsequent hydrolysis to give crude 2-chloro-2',4°-difluoro-4-biphenylylacetic acid which was converted to the methyl ester, m.p. 66°–67° C. (from 62–68 petroleum ether).

This was hydrolysed and recrystallised from 80–100 petroleum ether to give 2-chloro-2',4'-difluoro-4-biphenylylacetic acid, m.p. 114.5°–115.5° C.

EXAMPLE 23

A mixture of 2,2',4'-trifluoro-4-biphenylylacetamide (100 mg.), aqueous caustic soda (18N; 1 ml.) and water (5 ml.) was stirred under reflux overnight. The mixture was acidified and extracted with ether. The ether was evaporated and the product recrystallised from 80–100 petroleum ether to give 2,2',4'-trifluoro-4-biphenylylacetic acid, m.p. 144°–147° C.

EXAMPLE 24

A mixture of 2-[(2-chloro-2',4'-difluoro-4-biphenylyl)methyl]-4,4-dimethyl-2-oxazoline (100 mg.) and dilute hydrochloric acid (4 ml., 2.5N) was stirred under reflux overnight. The mixture was extracted with ether, the ether evaporated and the product recrystallised from 80–100 petroleum ether to give 2-chloro-2',4'-difluoro-4-biphenylylacetic acid, m.p. 113°–116° C.

EXAMPLE 25

A solution of 2-chloro-2',4'-difluoro-4-biphenylyl acetic acid (0.5 g.) and benzylamine (0.3 ml.) in dry ether (25 ml.) was stirred at room temperature for 15 minutes. The crystalline salt was collected, washed with ether and recrystallized from acetone/40–60 petroleum ether giving colourless needle clusters of benzylammonium 2-chloro-2',4'-difluoro-4-biphenylylacetate, m.p. 132°–133° C.

EXAMPLE 26

Aqueous caustic soda (18N:5 drops) was added to a solution of 2,2',4'-trifluoro-4-biphenylylacetic acid (0.8 g.) in acetone (5 ml.). After stirring for 5 hours, the precipitated solid was collected, washed with acetone and recrystallized from water giving colourless plates of sodium 2,2',4'-trifluoro-4-biphenylylacetate, m.p. 210°–212° C.

EXAMPLE 27

A solution of 2,2',4'-trifluoro-4-biphenylyl acetic acid (10 g.) in anhydrous methanol (100 ml.) and concentrated sulphuric acid (5 ml.) was refluxed overnight. Excess solvent was distilled and the residue was poured onto ice-water and extracted with ether. The extracts were washed with dilute aqueous sodium bicarbonate and then dried, evaporated and distilled to give a yellow oil, b.p. 142°–146°/0.5 mm., which solidified on cooling. This was crystallized from 62–68 petroleum ether to give methyl 2,2',4'-trifluoro-4-biphenylylacetate, m.p. 74°–77° C.

EXAMPLE 28

A solution of methyl 2,2',4'-trifluoro-4-biphenylyl acetate (1 g.) in dry ether (20 ml.) was added dropwise to a stirred suspension of lithium aluminium hydride (202 mg.) in ether (20 ml.). After a 90 minute reflux period excess reagent was decomposed with water and dilute sulphuric acid, and the product was isolated in ether. Evaporation and distillation afforded a colourless oil which solidified and was crystallized from 40–60 petroleum ether, to give 2-(2,2',4'-trifluoro-4-biphenylyl) ethanol, m.p. 44°–45° C.

EXAMPLE 29

A mixture of 2,2',4'-trifluoro-4-biphenylylacetic acid (3.6 g.) and thionyl chloride (15 ml.) was refluxed for 1 hour; excess thionyl chloride was removed and the residual acid chloride distilled at 141°–143° C./1.0 mm as a yellow oil, solidifying on cooling, (3.11 g.). Recrystallisation from 62–68 petroleum ether gave colourless needles of 2,2',4'-trifluoro-4-biphenylylacetyl chloride, m.p. 70°–73° C. 1 g. of this was dissolved in ether (10 ml.) and the solution added slowly to a stirred mixture of ammonia (SG = 0.880; 5 ml.) and ether (25 ml.) at room temperature. After stirring for 15 minutes, the product was isolated in ether, washed, dried and evaporated. Recrystallization of the residue from methylene chloride/40–60 petroleum ether followed by a further crystallization from 100–120 petroleum ether gave colourless plates of 2,2',4'-trifluoro-4-biphenylylacetamide, m.p. 137°–140° C.

EXAMPLE 30

Hydroxylamine free base was added to a solution of 2,2',4'-trifluoro-4-biphenylylacetyl chloride (obtained as in Example 9) in ether. After stirring for 15 minutes the ether solution was diluted with water, separated, washed again with water, dried and evaporated. The orange residue was recrystallised twice from acetone/40–60 petroleum ether and then from toluene to give fine colourless needles of 2,2',4'-trifluoro-4-biphenylylacethydroxamic acid, m.p. 149°–150° C.

EXAMPLE 31

The following mixture was formed into tablets in conventinal manner, each tablet containing 10 mg. of active ingredient.

|  | Parts |
| --- | --- |
| 2,2',4'-trifluoro-4-biphenylylacetic acid | 10 |
| maize starch | 30 |
| lactose | 163 |
| stearic acid | 1 |
| magnesium stearate | 1 |

EXAMPLE 32

Suppositories weighing 1 g. and containing 10 mg. of ethyl 2,2',4'-trifluoro-4-biphenylylacetate are prepared in a conventional manner using a base consisting of

| polyethylene glycol | 4000 | 33% |

| -continued | | |
|---|---|---|
| polyethylene glycol | 600 | 47% |
| water | | 20% |

Compositions similar to those described in Examples 31 and 32 are prepared containing as active ingredient the compounds of the invention described in Examples 22 to 30

We claim:

1. A compound selected from the group consisting of acids having the general formula:

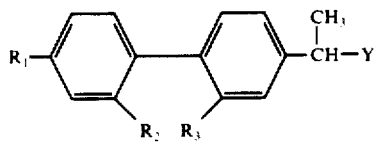

in which $R_1$, $R_2$ and $R_3$ are individually selected from chlorine, bromine and fluorine and Y is COOH, or a pharmaceutically acceptable lower-alkyl ester, in an alkali metal salt, or an amine salt thereof.

2. A compound according to claim 1 in which two of $R_1$, $R_2$ and $R_3$ are fluorine and the third is fluorine or chlorine.

3. A compound according to claim 1 in which at least two of $R_1$, $R_2$ and $R_3$ are fluorine.

4. A compound according to claim 1 in which $R_1$, $R_2$ and $R_3$ all represent fluorine.

5. A compound according to claim 1 in which two of $R_1$, $R_2$ and $R_3$ represent fluorine and one represents chlorine.

6. 2-(2,2',4'-Trifluoro-4-biphenylyl)propionic acid.

7. 2-(2-Chloro-2',4'-difluoro-4-biphenylyl)propionic acid.

8. 2-(2'-Chloro-2,4'-difluoro-4-biphenylyl)propionic acid.

9. 2-(4'-Chloro-2,2'-difluoro-4-biphenylyl)propionic acid.

10. A compound according to claim 1 in the form of an optically active isomer.

11. A therapeutic composition suitable for use in the treatment of inflammation comprising an effective anti-inflammatory amount of a compound according to claim 1 in association with a pharmaceutical excipient.

12. A therapeutic composition suitable for use in the treatment of inflammation in the form of tablets or capsules and comprising an effective anti-inflammatory amount of a compound according to claim 1.

13. A therapeutic composition suitable for use in the treatment of inflammation and suitable for rectal administration in the form of a suppository and comprising an effective anti-inflammatory amount of a compound according to claim 1.

14. A therapeutic composition suitable for use in the treatment of inflammation comprising an effective anti-inflammatory amount of a compound according to claim 4 in association with a pharmaceutical excipient.

15. A therapeutic composition suitable for use in the treatment of inflammation comprising an effective anti-inflammatory amount of a compound according to claim 5 in association with a pharmaceutical excipient.

16. A therapeutic composition according to claim 11 in dosage form suitable for therapeutic administration comprising 0.5 to 500 mg. of said compound per unit.

17. A method of treating inflammation in a patient comprising administering an effective amount of a compound according to claim 1.

18. A method of treating inflammation in a patient comprising administering not more than twice a day an effective amount of a compound according to claim 1.

19. A method of treating inflammation in a patient comprising administering not more than twice a day an effective amount of a compound according to claim 4.

20. A method of treating inflammation in a patient comprising administering not more than twice a day an effective amount of a compound according to claim 5.

* * * * *